US008923562B2

(12) United States Patent
Lin et al.

(10) Patent No.: US 8,923,562 B2
(45) Date of Patent: Dec. 30, 2014

(54) THREE-DIMENSIONAL INTERACTIVE DEVICE AND OPERATION METHOD THEREOF

(71) Applicant: Industrial Technology Research Institute, Hsinchu (TW)

(72) Inventors: Hung-Wei Lin, Chiayi County (TW); Hau-Wei Wang, Taipei (TW); Shu-Ping Dong, Taichung County (TW)

(73) Assignee: Industrial Technology Research Institute, Hsinchu (TW)

( * ) Notice: Subject to any disclaimer, the term of this patent is extended or adjusted under 35 U.S.C. 154(b) by 78 days.

(21) Appl. No.: 13/895,382

(22) Filed: May 16, 2013

(65) Prior Publication Data

US 2014/0177909 A1 Jun. 26, 2014

(30) Foreign Application Priority Data

Dec. 24, 2012 (TW) .............................. 101149581 A

(51) Int. Cl.
*G06K 9/00* (2006.01)
*G06F 3/01* (2006.01)
*G06F 19/00* (2011.01)

(52) U.S. Cl.
CPC ............ *G06F 3/017* (2013.01); *G06K 9/00355* (2013.01); *G06F 19/00* (2013.01)
USPC ............................ 382/103; 348/169; 715/863

(58) Field of Classification Search
USPC ......... 382/100, 103, 107, 181, 190, 195, 203; 348/135, 169–172; 715/863
See application file for complete search history.

(56) References Cited

U.S. PATENT DOCUMENTS

| 6,160,899 | A  | * | 12/2000 | Lee et al. ....................... 382/103 |
| 6,176,782 | B1 | * | 1/2001  | Lyons et al. ..................... 463/36 |
| 7,022,971 | B2 |   | 4/2006  | Ura et al. |
| 7,274,800 | B2 |   | 9/2007  | Nefian et al. |
| 7,340,077 | B2 |   | 3/2008  | Gokturk et al. |

(Continued)

FOREIGN PATENT DOCUMENTS

| TW | 200725380 | 7/2007 |
| TW | 201037574 | 10/2010 |
| TW | 201228357 | 7/2012 |

OTHER PUBLICATIONS

"Office Action of Taiwan Counterpart Application", issued on Jul. 31, 2014, p. 1-p. 3.

(Continued)

*Primary Examiner* — Anand Bhatnagar
(74) *Attorney, Agent, or Firm* — Jianq Chyun IP Office

(57) ABSTRACT

A three-dimensional (3D) interactive device and an operation method thereof are provided. The 3D interactive device includes a projection unit, an image capturing unit, and an image processing unit. The projection unit projects an interactive pattern to a surface of a body, so that a user performs an interactive trigger operation on the interactive pattern by a gesture. The image capturing unit captures a depth image within an image capturing range. The image processing unit receives the depth image and determines whether the depth image includes a hand region of the user. If yes, the image processing unit performs hand geometric recognition on the hand region to obtain gesture interactive semantics. According to the gesture interactive semantics, the image processing unit controls the projection unit and the image capturing unit. Accordingly, the disclosure provides a portable, contact-free 3D interactive device.

21 Claims, 6 Drawing Sheets

(56) References Cited

U.S. PATENT DOCUMENTS

| | | |
|---|---|---|
| 7,379,563 B2 | 5/2008 | Shamaie |
| 7,414,705 B2 | 8/2008 | Boillot |
| 7,620,316 B2 | 11/2009 | Boillot |
| 7,665,041 B2 | 2/2010 | Wilson et al. |
| 7,724,355 B1 | 5/2010 | McIntosh et al. |
| 7,725,288 B2 | 5/2010 | Boillot |
| 7,788,607 B2 | 8/2010 | Boillot |
| 7,834,305 B2 | 11/2010 | Hagio et al. |
| 7,834,847 B2 | 11/2010 | Boillot et al. |
| 7,834,850 B2 | 11/2010 | Boillot et al. |
| 7,863,551 B2 | 1/2011 | Bang et al. |
| 7,924,441 B1 | 4/2011 | Milanovi |
| 7,961,173 B2 | 6/2011 | Boillot |
| 7,978,091 B2 | 7/2011 | Boillot |
| 8,050,461 B2 | 11/2011 | Shpunt et al. |
| 8,060,841 B2* | 11/2011 | Boillot et al. ............ 715/863 |
| 8,139,029 B2 | 3/2012 | Boillot et al. |
| 8,150,142 B2 | 4/2012 | Freedman et al. |
| 8,166,421 B2 | 4/2012 | Magal et al. |
| 8,169,404 B1 | 5/2012 | Boillot |
| 8,180,114 B2 | 5/2012 | Nishihara et al. |
| 8,199,108 B2 | 6/2012 | Bell |
| 8,228,315 B1* | 7/2012 | Starner et al. ............ 345/175 |
| 8,230,367 B2* | 7/2012 | Bell et al. ................ 715/863 |
| 8,249,334 B2 | 8/2012 | Berliner et al. |
| 8,345,920 B2* | 1/2013 | Ferren et al. ............. 382/103 |
| 8,427,511 B2* | 4/2013 | Shin et al. ............... 345/661 |
| 8,818,027 B2* | 8/2014 | Forutanpour et al. ..... 382/103 |
| 2002/0186221 A1 | 12/2002 | Bell |
| 2003/0132913 A1 | 7/2003 | Issinski |
| 2005/0276444 A1 | 12/2005 | Zhou et al. |
| 2007/0120834 A1 | 5/2007 | Boillot |
| 2007/0121097 A1 | 5/2007 | Boillot |
| 2007/0125633 A1 | 6/2007 | Boillot |
| 2007/0126696 A1 | 6/2007 | Boillot |
| 2007/0130547 A1 | 6/2007 | Boillot |
| 2007/0211022 A1 | 9/2007 | Boillot |
| 2007/0211023 A1 | 9/2007 | Boillot |
| 2007/0288194 A1 | 12/2007 | Boillot |
| 2008/0013793 A1 | 1/2008 | Hillis et al. |
| 2008/0048878 A1 | 2/2008 | Boillot |
| 2008/0055247 A1 | 3/2008 | Boillot |
| 2008/0059915 A1 | 3/2008 | Boillot |
| 2008/0100572 A1 | 5/2008 | Boillot |
| 2008/0111710 A1 | 5/2008 | Boillot |
| 2008/0204834 A1 | 8/2008 | Hill |
| 2008/0244468 A1 | 10/2008 | Nishihara et al. |
| 2009/0172606 A1 | 7/2009 | Dunn et al. |
| 2009/0316952 A1* | 12/2009 | Ferren et al. ............. 382/103 |
| 2010/0001994 A1 | 1/2010 | Kim et al. |
| 2010/0013763 A1 | 1/2010 | Futter et al. |
| 2010/0013944 A1 | 1/2010 | Venetsky et al. |
| 2010/0020078 A1 | 1/2010 | Shpunt |
| 2010/0039500 A1 | 2/2010 | Bell et al. |
| 2010/0050133 A1 | 2/2010 | Nishihara et al. |
| 2010/0050134 A1 | 2/2010 | Clarkson |
| 2010/0060583 A1 | 3/2010 | Yan |
| 2010/0060722 A1 | 3/2010 | Bell |
| 2010/0118123 A1 | 5/2010 | Freedman et al. |
| 2010/0194679 A1 | 8/2010 | Wu et al. |
| 2010/0231509 A1 | 9/2010 | Boillot et al. |
| 2010/0265316 A1 | 10/2010 | Sali et al. |
| 2010/0284082 A1 | 11/2010 | Shpunt et al. |
| 2010/0290698 A1 | 11/2010 | Freedman et al. |
| 2010/0304854 A1 | 12/2010 | McEldowney |
| 2011/0019205 A1 | 1/2011 | Gerber et al. |
| 2011/0025827 A1 | 2/2011 | Shpunt et al. |
| 2011/0025843 A1 | 2/2011 | Oggier et al. |
| 2011/0041100 A1 | 2/2011 | Boillot |
| 2011/0051118 A1 | 3/2011 | Sato et al. |
| 2011/0052006 A1 | 3/2011 | Gurman et al. |
| 2011/0077757 A1 | 3/2011 | Chang et al. |
| 2011/0085704 A1 | 4/2011 | Han et al. |
| 2011/0090147 A1 | 4/2011 | Gervais et al. |
| 2011/0096072 A1 | 4/2011 | Kim et al. |
| 2011/0096182 A1 | 4/2011 | Cohen et al. |
| 2011/0109577 A1 | 5/2011 | Lee et al. |
| 2011/0114857 A1 | 5/2011 | Akerman et al. |
| 2011/0154249 A1* | 6/2011 | Jang et al. ................ 715/781 |
| 2011/0158508 A1 | 6/2011 | Shpunt et al. |
| 2011/0164029 A1 | 7/2011 | King et al. |
| 2011/0164191 A1 | 7/2011 | Brown |
| 2011/0181553 A1 | 7/2011 | Brown et al. |
| 2011/0221750 A1 | 9/2011 | Sato et al. |
| 2011/0228251 A1 | 9/2011 | Yee et al. |
| 2011/0286676 A1 | 11/2011 | El Dokor |
| 2011/0291988 A1 | 12/2011 | Bamji et al. |
| 2012/0001875 A1 | 1/2012 | Li et al. |
| 2012/0013222 A1 | 1/2012 | Herzog et al. |
| 2012/0013529 A1 | 1/2012 | McGibney et al. |
| 2012/0038986 A1 | 2/2012 | Pesach |
| 2012/0056804 A1* | 3/2012 | Radivojevic et al. ...... 345/156 |
| 2012/0056852 A1 | 3/2012 | Lee et al. |
| 2012/0062736 A1* | 3/2012 | Xiong ....................... 348/143 |
| 2012/0093360 A1 | 4/2012 | Subramanian et al. |
| 2012/0113223 A1 | 5/2012 | Hilliges et al. |
| 2012/0113241 A1 | 5/2012 | Sundaresan et al. |
| 2012/0117514 A1 | 5/2012 | Kim et al. |
| 2012/0119987 A1 | 5/2012 | Im et al. |
| 2012/0120073 A1 | 5/2012 | Haker et al. |
| 2012/0127273 A1 | 5/2012 | Zhang et al. |
| 2012/0133584 A1 | 5/2012 | Lee et al. |
| 2012/0133585 A1 | 5/2012 | Han et al. |
| 2012/0169583 A1 | 7/2012 | Rippel et al. |
| 2012/0184854 A1 | 7/2012 | Raju et al. |
| 2012/0194650 A1 | 8/2012 | Izadi et al. |
| 2013/0283208 A1* | 10/2013 | Bychkov et al. .......... 715/810 |

OTHER PUBLICATIONS

Woods et al, "Image Distortions in Stereoscopic Video Systems," Proceedings of the SPIE vol. 1915 Stgereoscopic Displays and Applications IV, Feb. 1993, pp. 1-13.

Hamer et al., "Tracking a Hand Manipulating an Object," IEEE Computer Vision, Sep. 2009, pp. 1-8.

Cyganek et al., "An Introduction to 3D Computer Vision Techniques and Algorithms," Wiley, Mar. 2009, pp. xv-483.

Elmezain et al., "A Robust Method for Hand Tracking Using Meanshift Altorithm and Kalman Filter in Stereo Color Image Sequences," World Academy of Science, Engineering and Technology 59, Nov. 2009, pp. 283-287.

Wang et al., "Real-Time Hand-Tracking with a Color Glove," ACM Transactions on Graphics (TOG)—Proceedings of ACM SIGGRAPH, Aug. 2009, pp. 1-8.

* cited by examiner

THREE-DIMENSIONAL INTERACTIVE DEVICE AND OPERATION METHOD THEREOF

CROSS-REFERENCE TO RELATED APPLICATION

This application claims the priority benefit of Taiwan application serial no. 101149581, filed on Dec. 24, 2012. The entirety of the above-mentioned patent application is hereby incorporated by reference herein and made a part of this specification.

TECHNICAL FIELD

The disclosure relates to a three-dimensional (3D) interactive device and an operation method thereof

BACKGROUND

In recent years, contact-free human-machine interfaces (cfHMIs) have been developed rapidly. According to the research paper authored by an analyst from Forrester Research, Inc., as long as the motion sensing technology that revolutionizes human beings' interactions with electronic devices has fully crept into our daily lives, it will present us a vision of future interactive experiences. At present, a number of manufacturers have been dedicated to creating various products that may be applied in our daily lives. For instance, Kinect, the new era motion sensing input device launched by Microsoft, enables gamers to interact with the console by means of human gestures and movements without the need to touch a game controller; at the exhibition hall of Boeing, an interactive virtual simulator allows people to experience 3D flight simulation.

Depth images provide complete spatial image information, and therefore how to effectively, timely, and stably obtain the information of the third dimension (i.e., the depth) is essential to the development of interactive virtual input technologies. According to the related art, a depth map technology that may achieve "spatial 3D interaction" has drawn most of the attention, whereas the absolute coordinate of hand motion and even delicate finger motion can be barely obtained through the depth map estimation due to the existing limitations of distance, resolution, and so on. As such, it is rather difficult to apply the depth map technology to meet small-range cfHMI requirements.

The existing interactive input devices are mostly applied for human-machine interactions within a wide range, such as a large-sized immersive interactive virtual device, an interactive digital blackboard, a motion-sensing interactive game, and so forth, whereas an object moving within a rather small range in the 3D space is not apt to be accurately positioned. For instance, the existing interactive input technology is not suitable for being applied to capture fine and short-ranged motions of hand-sized objects. Although some interactive devices equipped with handheld infrared projectors or markers may track and recognize users' gestures or motions, these interactive devices are merely applicable in case of the wide interaction range. Subject to the fixed projection image area and the imprecise dimensions of markers, the conventional interactive technologies are not yet applicable to a portable, contact-free 3D human-machine interactive interface that may capture short-range motions.

SUMMARY

In an exemplary embodiment of the disclosure, a 3D interactive device that includes a projection unit, an image capturing unit, and an image processing unit is provided. The projection unit projects an interactive pattern to a surface of a body, such that a user performs an interactive trigger operation on the interactive pattern by a gesture. Here, the interactive pattern is projected within a projection range. The image capturing unit captures a depth image within an image capturing range, and the image capturing range covers the projection range. The image processing unit is connected to the projection unit and the image capturing unit. Besides, the image processing unit receives the depth image and determines whether the depth image includes a hand region of the user. If yes, the image processing unit performs hand geometric recognition on the hand region to obtain gesture interactive semantics. According to the gesture interactive semantics, the image processing unit controls the projection unit and the image capturing unit.

In another exemplary embodiment of the disclosure, an operation method of a 3D interactive device is provided, and the 3D interactive device includes a projection unit and an image capturing unit. The operation method includes following steps. A coordinate calibration process is performed on a projection coordinate of the projection unit and an image capturing coordinate of the image capturing unit. An interactive pattern is projected to a surface of a body by the projection unit, such that a user performs an interactive trigger operation on the interactive pattern by a gesture. Here, the interactive pattern is projected within a projection range. A depth image within an image capturing range is captured by the image capturing unit, and the image capturing range covers the projection range. Whether the depth image includes a hand region of the user is determined. If yes, hand geometric recognition is performed on the hand region to obtain gesture interactive semantics. The projection unit and the image capturing unit are controlled according to the gesture interactive semantics.

Several exemplary embodiments accompanied with figures are described in detail below to further describe the disclosure in details.

BRIEF DESCRIPTION OF THE DRAWINGS

The accompanying drawings are included to provide further understanding, and are incorporated in and constitute a part of this specification. The drawings illustrate exemplary embodiments and, together with the description, serve to explain the principles of the disclosure.

DETAILED DESCRIPTION OF DISCLOSED EMBODIMENTS

In the three-dimensional (3D) interactive device described in the exemplary embodiment, the design of an image capturing unit/device and a design of a projection unit/device are combined, and a technique of calibrating a projection coordinate and an image capturing coordinate is applied, such that the portable 3D interactive device described herein may achieve contact-free interactive input effects. Since a target object is recognized and tracked by means of a depth image, the 3D interactive device that experiences environmental changes and background light variations is resistant to light and is able to prevent the ambient light interference. Besides, the user who employs the 3D interactive device described herein need not wear markers, and the 3D interactive device can still perform the gesture recognition function and is capable of positioning fingertips of a user in the 3D space, thus ensuring the contact-free interaction between the device and the user's motion within a small range (e.g., the size of a hand portion). The portable contact-free 3D interactive device is able to locate a coordinate of motion of an object within a small range, so as to achieve the 3D spatial interaction effects through projecting an interactive pattern to any location.

In order to make the disclosure more comprehensible, several exemplary embodiments are described below. The exemplary embodiments provided herein are explanatory and do not serve to limit the scope of the disclosure.

Figure 1:
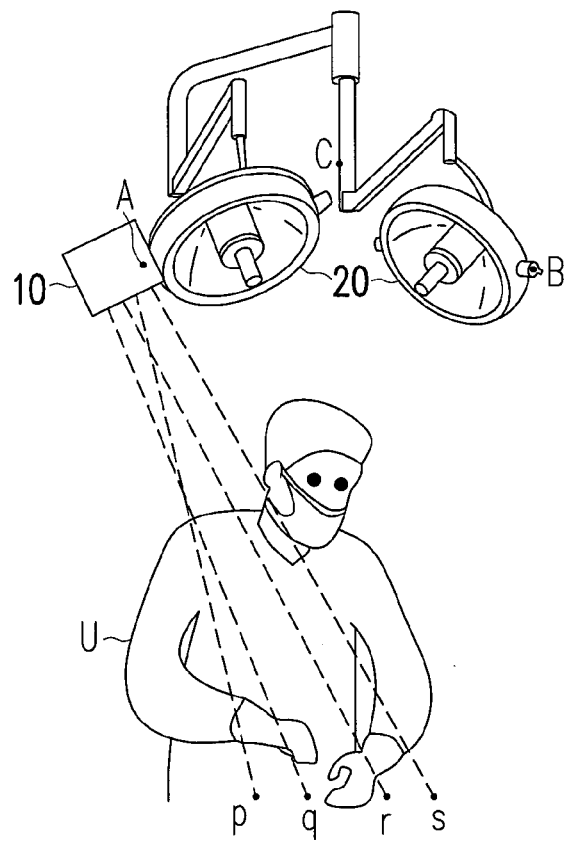
FIG. 1 is a schematic view of applying a three-dimensional (3D) interactive device according to an exemplary embodiment of the disclosure.

In the disclosure, the 3D interactive device may be integrated into an operation medical device, for instance, such that the medical device can provide not only the input function through pressing contact-type physical keys but also the function of positioning fingertips in the 3D space. Thereby, paramedics are able to control and operate the medical device in a contact-free manner, thus lowering the possibility of bacteria infection caused by human contact. FIG. 1 is a schematic view of applying a 3D interactive device according to an exemplary embodiment of the disclosure. With reference to FIG. 1, the 3D interactive device 10 is placed and fixed at a position A where an operation lamp 20 is located, for instance, and the 3D interactive device 10 may also be placed at a position B or a position C, which should however not be construed as a limitation to the disclosure. The actual position of the 3D interactive device 10 may be determined according to actual application requirements. Besides, the 3D interactive device 10 may also be placed on other medical instruments in addition to the operation lamp.

In the exemplary embodiment of the disclosure, the 3D interactive device 10 at least includes a projection unit and an image capturing unit (that are not shown in FIG. 1). The projection unit may project an interactive pattern (e.g., any pattern interface including a pattern of a press button) to a position where a hand portion (e.g., a palm or an arm) of a user U is located, and the image capturing unit captures a depth image of the hand portion of the user U who interacts with the device. If the operation lamp 20 is relocated, or there is a change to the angle at which the operation lamp 20 is placed, the projection location of the projection unit and the image capturing location of the image capturing unit are also changed. As shown in FIG. 1, the distance from the point p to the point s represents the maximum horizontal axial image capturing range of the image capturing unit; the distance from the point q to the point r represents the maximum horizontal axial projection range of the projection unit.

Although the angle change or the position change of the operation lamp 20 may pose an impact on the image capturing location or the projection location of the 3D interactive device 10, the 3D interactive device 10 may continuously capture the depth image that covers the hand portion of the user U by means of the image capturing unit and further recognize the coordinate of the hand portion, such that the projection unit is allowed to project the interactive pattern to the hand portion of the user U. The size of the hand portion of the user U is approximately 10 cm×10 cm (i.e., a small range of area). The 3D interactive device 10 may also accurately analyze the variations in hand gestures and movement of the user U, interpret the gesture interactive semantics of the gestures and movement, and thereby present the result of interaction.

Figure 2:
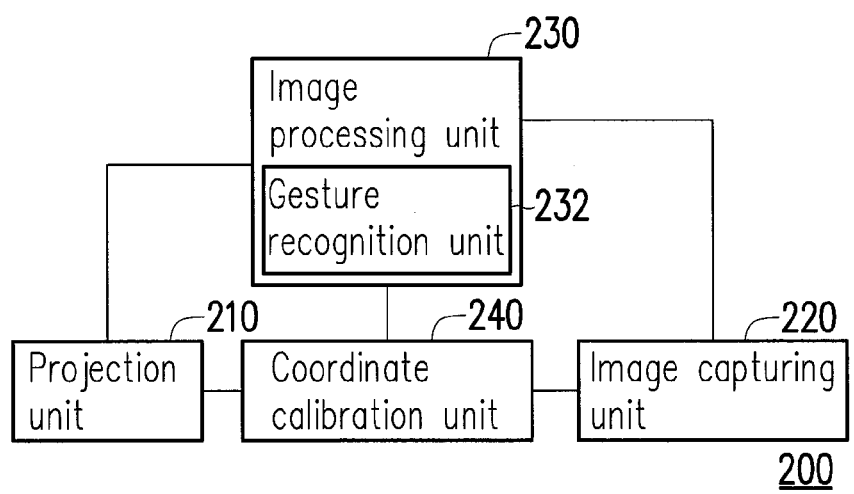
FIG. 2 is a block view illustrating a 3D interactive device according to an exemplary embodiment of the disclosure.

The detailed way to implement the 3D interactive device 10 shown in FIG. 1 is explained in the following exemplary embodiment. FIG. 2 is a block view illustrating a 3D interactive device according to an exemplary embodiment of the disclosure.

With reference to FIG. 2, the 3D interactive device 200 at least includes a projection unit 210, an image capturing unit 220, an image processing unit 230, a gesture recognition unit 232, and a coordinate calibration unit 240. The exemplary functions of these components are respectively described below.

The projection unit 210 projects an interactive pattern to a surface of a body. The body may, for instance, refer to a projection screen, human body parts, a user's hand portion, an operation table, a hospital bed, a working table, a desktop, a wall, a notebook, a piece of paper, a wooden board, or any other object on which the interactive pattern may be projected; however, the disclosure is not limited thereto. In an exemplary embodiment, the projection unit 210 may be a pico-projector (also referred to as a mini projector), for instance. In general, the pico-projector uses a light emitting diode (LED) or other solid-state optical sources as its light source, so as to increase the needed lumen and further increase the brightness of the image projected by the pico-projector. The dimension of the pico-projector is similar to that of a normal consumer mobile phone. Therefore, the pico-projector is portable and can be used anywhere, and thus the pico-projector is suitable for being utilized in the 3D interactive device 200 described herein.

For instance, the projection unit 210 may have different specifications and may be "BENQ Jobee GP2" (trade name) with the 44 inches short-distance projection function and the brightness of 200 lumens, "ViewSonic high-definition palm-sized LED projector PLED-W200" (trade name) with the design of 40 inches short focal projection and the brightness of 250 lumens, or "i-connect ViewX" (trade name) laser pico-projector. The products exemplified above are examples of the projection unit 210 and should not be construed as limitations to the disclosure.

In an exemplary embodiment, the image capturing unit 220 may be a "depth image camera" which not only takes two-dimensional pictures but also emits infrared light. By calculating the time frame during which the infrared light is in contact with and is reflected by the to-be-shot object, the depth image camera may determine the distance from the object to the camera itself and thus obtain a depth image/depth map indicating the distance to the object. According to an exemplary embodiment, the image capturing unit 220 may be a contact-free depth camera with the active scanning specification.

For instance, the image capturing unit 220 may have different specifications and may be a time-of-flight camera, a stereo vision depth camera, a laser speckle camera, a laser tracking camera, and so forth.

The image processing unit 230 may be implemented in form of software, hardware, or a combination thereof, which should not be construed as a limitation to the disclosure. The software may refer to application software or a driver, for instance. The hardware may refer to a central processing unit (CPU), a general or specific programmable microprocessor, a digital signal processor (DSP), and so on, for instance.

The image processing unit 230 may further include a gesture recognition unit 232 which not only can identify the hand region of the user in the depth image captured by the image capturing unit 220 but also can recognize the geometrical shape of the hand region of the user. Through comparing a sample in a gesture interactive semantic database (not shown in FIG. 2) with the geometrical shape of the hand region of the user, the image processing unit 230 is able to recognize the gesture interactive semantics. In the exemplary embodiment, the gesture interaction is merely exemplary, and the interaction may be achieved by means of other objects, such as a pen, a stick, and so forth. In this case, an object interaction database may be established for comparison.

The coordinate calibration unit 240 is coupled to the projection unit 210 and the image capturing unit 220 for calibrating a projection coordinate of the projection unit 210 and an image capturing coordinate of the image capturing unit 220. The calibration method will be elaborated hereinafter.

Figure 3A:
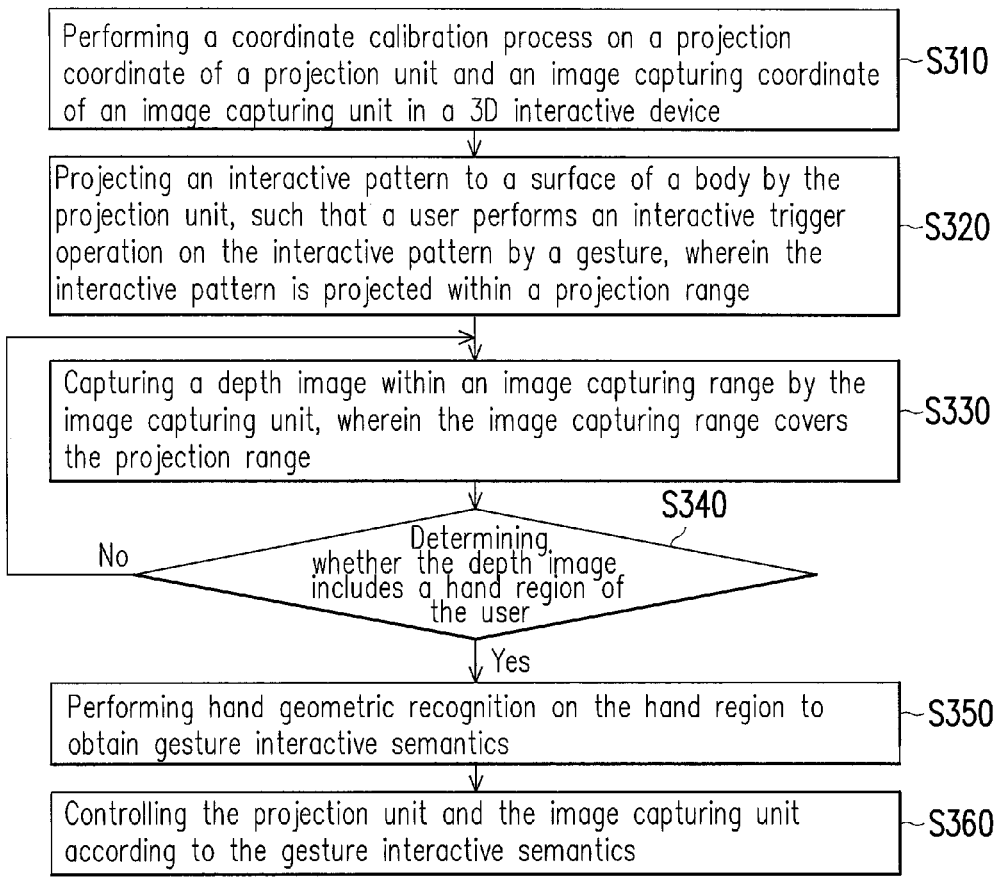
FIG. 3A is a flowchart illustrating an operation method of a 3D interactive device according to an exemplary embodiment of the disclosure.

FIG. 3A is a flowchart illustrating an operation method of a 3D interactive device according to an exemplary embodiment of the disclosure. The operation method described in the exemplary embodiment is adapted to the 3D interactive device 200 shown in FIG. 2, and the steps in the operation method are explained hereinafter with reference to the components in the 3D interactive device 200.

In step S310, the coordinate calibration unit 240 performs a coordinate calibration process on a projection coordinate of the projection unit 210 and an image capturing coordinate of the image capturing unit 220 in the 3D interactive device 200. After a coordinate transformation between the projection coordinate and the image capturing coordinate is obtained, in step S320, the projection unit 210 projects a first interactive pattern to a surface of a body, such that a user performs an interactive trigger operation on the first interactive pattern by a gesture. Here, the first interactive pattern is projected within a predetermined projection range. According to the exemplary embodiment, the body may, for instance, refer to a user's hand, human body parts, a surface of a platform, a projection screen, an operation table, a hospital bed, a working table, a desktop, a wall, a notebook, a piece of paper, a wooden board, or any other object on which the first interactive pattern may be projected; however, the disclosure is not limited thereto.

In step S330, the image capturing unit 220 captures a depth image within an image capturing range, and the image capturing range covers the projection range. After the depth image is captured, in step S340, the image processing unit 230 determines whether the depth image includes a hand region of the user through the gesture recognition unit 232. If yes, hand geometric recognition is performed on the hand region to obtain gesture interactive semantics (step S350). In step S360, the image processing unit 230 controls the projection unit 210 and the image capturing unit 220 according to the gesture interactive semantics. In an exemplary embodiment, the image processing unit 230 may control the projection unit 210 to project a second interactive pattern (i.e., a resultant interaction pattern) according to the gesture interactive semantics to the surface of the body, so as to continue the interaction. The image processing unit 230 may also control the image capturing unit 220 to continuously capture the depth image that contains the gesture of the user.

Figure 3B:
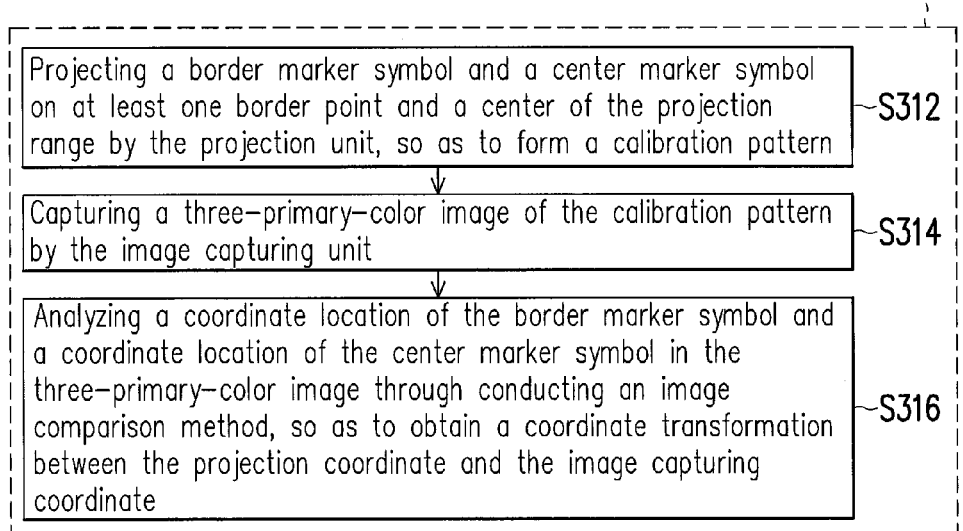
FIG. 3B is a flowchart illustrating a coordinate calibration process according to an exemplary embodiment of the disclosure.
Figure 4:
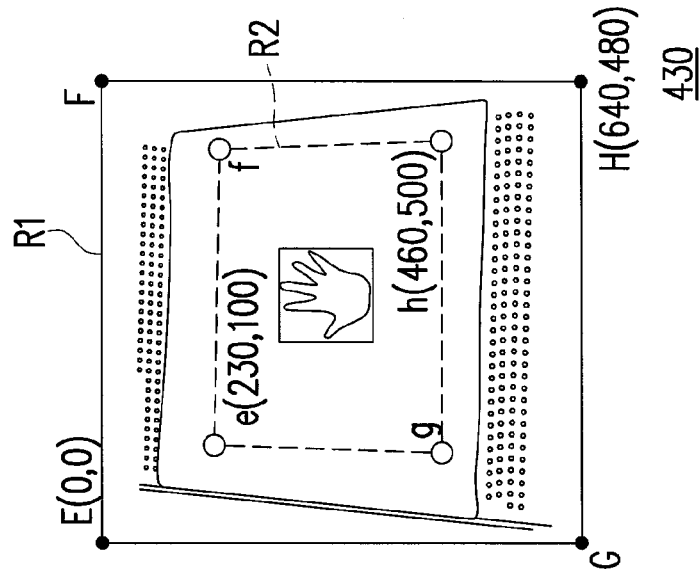
FIG. 4 is a schematic brief view illustrating a coordinate calibration process according to an exemplary embodiment of the disclosure.
Figure 4:
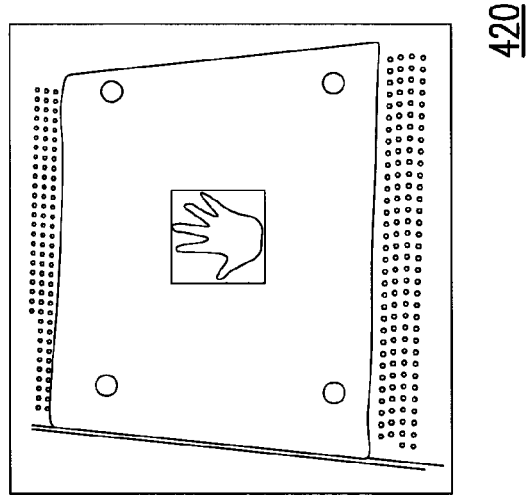
Figure 4:
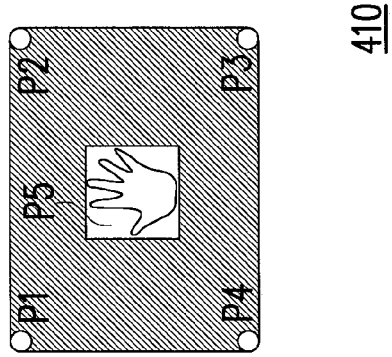

The coordinate calibration process performed by the coordinate calibration unit 240 as described in step S310 is elaborated hereinafter. FIG. 3B is a flowchart illustrating a coordinate calibration process according to an exemplary embodiment of the disclosure. FIG. 4 is a schematic brief view illustrating a coordinate calibration process according to an exemplary embodiment of the disclosure. Please refer to FIG. 3B and FIG. 4.

In an exemplary embodiment, the coordinate calibration process may be divided into several steps S312, S314, and S316. The projection unit 210 respectively projects a border marker symbol and a center marker symbol on at least one border point and a center of the projection range, so as to form a set calibration pattern (step S312). According to the exemplary embodiment, the border marker symbol is a pattern of a circular point, for instance, and the center marker symbol is a hand-shaped pattern, for instance. However, the disclosure is not limited thereto, and both the border marker symbol and the center marker symbol may be shaped at will. As shown in FIG. 4, the image 410 exhibits the calibration pattern projected by the projection unit 210 and includes four patterns P1, P2, P3, and P4 of circular points. The hand-shaped pattern P5 is projected to the center of the image 440. The four patterns P1, P2, P3, and P4 of circular points serve to mark the maximum boundary where the projection unit 210 is able to project patterns. The hand-shaped pattern P5 may serve to remind the user of the following interactive trigger operation by his or her gesture, for instance.

In step S314, the image capturing unit 220 captures a three-primary-color image of the calibration pattern. During the coordinate calibration process, the image capturing unit 220 serves to capture the three-primary-color image (i.e., the RGB image) instead of the depth image. Since the depth image has the function of providing depth information, the three-primary-color image of the calibration pattern has to be further obtained. With reference to FIG. 4, the image 420 exhibits the three-primary-color image that is captured by the image capturing unit 220 and then undergoes binary treatment and edge treatment. The image capturing unit 220 not only captures the calibration pattern but also takes the pictures of background objects, e.g., a working platform.

Through conducting an image comparison method, the coordinate calibration unit 240 analyzes a coordinate of the border marker symbol and a coordinate of the center marker symbol in the three-primary-color image, so as to obtain a coordinate transformation between the projection coordinate and the image capturing coordinate (step S316). The image comparison method includes but is not limited to a chamfer distance image comparison method. Any image comparison method that is suitable for analyzing and comparing the border marker symbol and the center marker symbol can be applied in this step.

As shown in FIG. 4, the image 430 exhibits coordinates E, F, G, and H, and the region R1 defined by the coordinates E, F, G, and H is the image capturing range of the image capturing unit 220. The coordinate E(0,0) is the origin of the image capturing unit 220, and the coordinate H(640,480) indicates that the dimension of the image captured by the image capturing unit 220 is 640×480 (pixels). The region R2 defined by coordinates e, f, g, and h is the projection range of the projection unit 210. The coordinate e(230,100) is the origin of the projection unit 210, and the difference obtained by subtracting the coordinate e(230,100) from the coordinate h(460,500) indicates that the maximum dimension of the image projected by the projection unit 210 is 230×400 (pixels). Thereby, the coordinate calibration unit 240 is able to learn the coordinate transformation between the projection coordinate and the image capturing coordinate.

Figure 5:
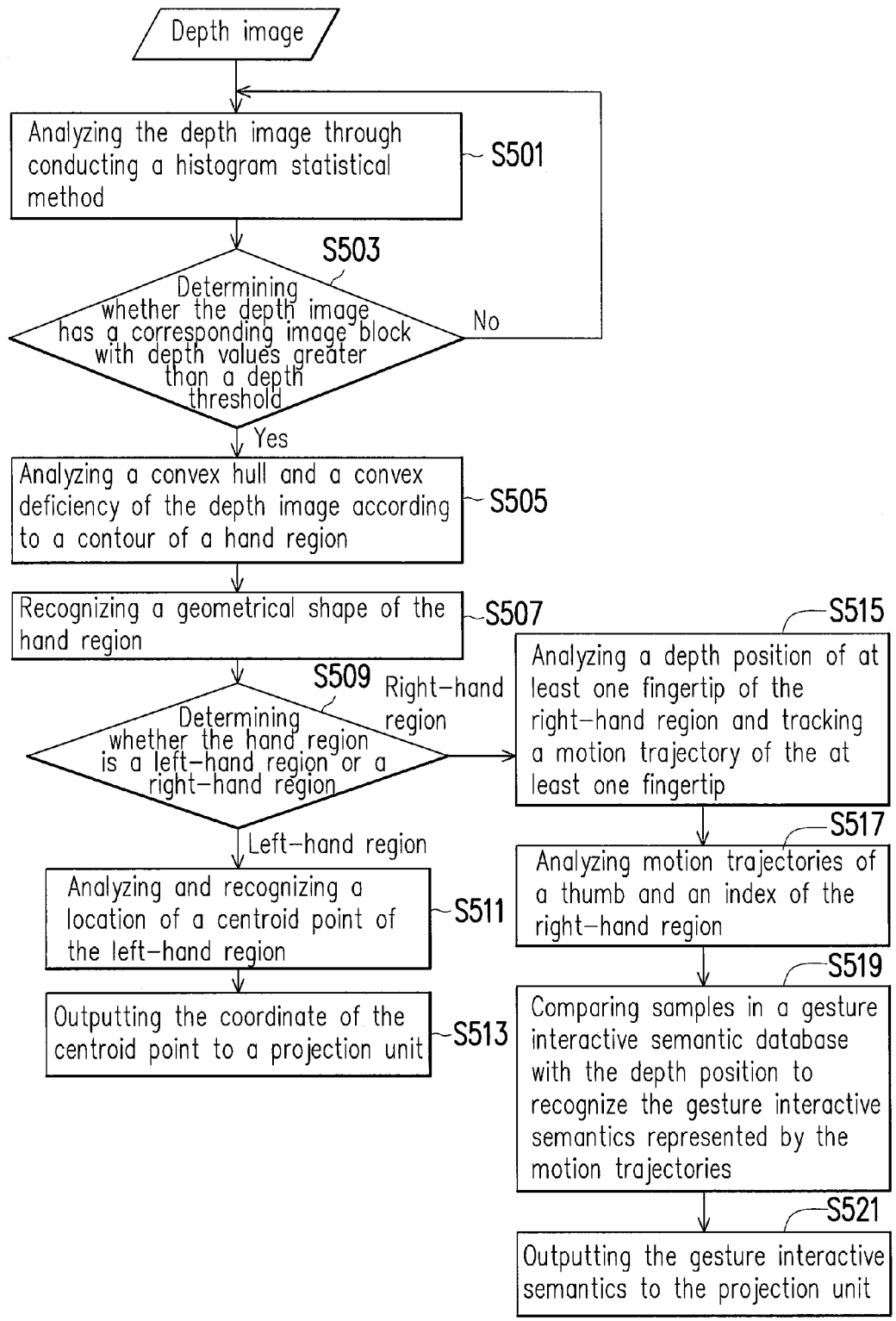
FIG. 5 is a flowchart illustrating a method of obtaining gesture interactive semantics through a gesture recognition unit according to another exemplary embodiment of the disclosure.

Another exemplary embodiment is provided hereinafter to elaborate the detailed steps S340 and S350 performed by the gesture recognition unit 232 shown in FIG. 3A. FIG. 5 is a flowchart illustrating a method of obtaining gesture interactive semantics through a gesture recognition unit according to another exemplary embodiment of the disclosure.

With reference to FIG. 5, after receiving the depth image, the gesture recognition unit 232 analyzes the depth image through conducting a histogram statistical method (step S501). Each pixel or each block of the depth image has a corresponding depth value. For instance, the closer the user's hand to the image capturing unit 220, the smaller the depth value; the farther the user hand away from the image capturing unit 220, the larger the depth value. In this step, the horizontal axis of the depth histogram represents the depth values, and the vertical axis represents the corresponding number of pixels.

It is determined whether the depth image has a corresponding image block with the depth values greater than a depth threshold, so as to determine whether the depth image includes a hand region of the user (step S503). The depth threshold is set as 200, for instance.

Figure 6A:
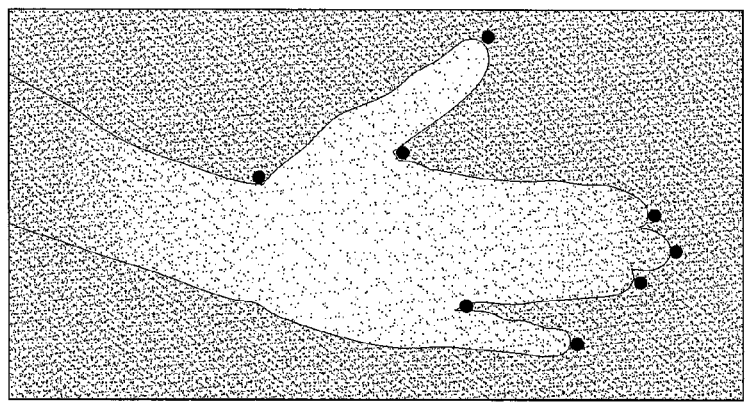
FIG. 6A is a schematic view of analyzing a convex hull and a convex deficiency in a depth image.

If the depth image includes the hand region of the user, a convex hull and a convex deficiency of the depth image are analyzed according to a contour of the hand region (step S505). FIG. 6A is a schematic view of analyzing a convex hull and a convex deficiency in a depth image.

The information regarding the convex hull and the convex deficiency of the depth image may be applied to recognize the geometrical shape of the hand region (step S507). It is then determined whether the hand region is the left-hand region or the right-hand region of the user (step S509). If it is determined that the hand region is the left-hand region, the projection unit 210 may project the interactive pattern to the left palm of the user; thus, in the following step S511, a location of a centroid point of the hand region (i.e., the left-hand region) of the user is analyzed and recognized. In step S513, the coordinate calibration unit 240 outputs the location of the centroid point to the projection unit 210. According to the coordinate of the centroid point, the projection unit 210 is capable of correspondingly adjusting a projection location of the interactive pattern or adjusting a dimension of the interactive pattern. That is, in an exemplary embodiment, the projection unit 210 accurately projects the interactive pattern to the left hand of the user, and the user is able to perform the interactive trigger operation on the interactive pattern projected to his or her left hand by the gesture of his or her right hand.

Figure 6B:
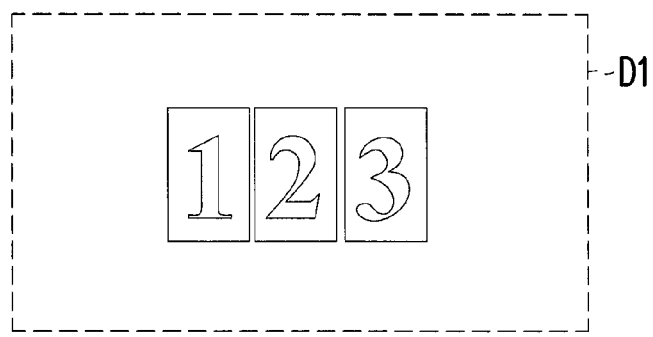
FIG. 6B is a schematic view illustrating an interactive pattern projected by a projection unit according to an exemplary embodiment of the disclosure.
Figure 6C:
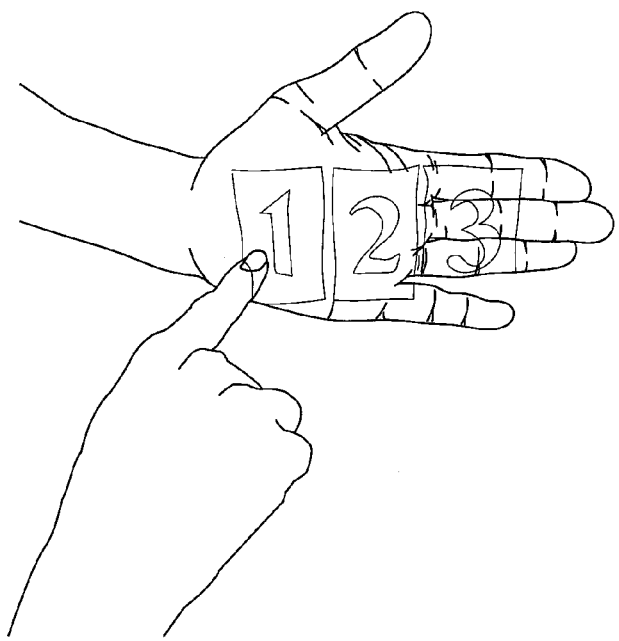
FIG. 6C schematically illustrates an application scenario of a projection unit projecting an interactive pattern to a hand region of a user according to an exemplary embodiment of the disclosure.

FIG. 6B is a schematic view illustrating an interactive pattern projected by a projection unit according to an exemplary embodiment of the disclosure. The dotted line D1 represents the possible projection range of the projection unit. FIG. 6C schematically illustrates an application scenario of a projection unit projecting an interactive pattern to a left-hand region of a user according to an exemplary embodiment of the disclosure. The projection unit 210, after obtaining the coordinate of the centroid point of the hand region, projects the interactive pattern shown in FIG. 6B to the hand region of the user. When the user's hand moves, the projection unit 210 may change the projection location correspondingly.

In step S509, if it is determined that the hand region is the right-hand region, it indicates that the user performs the interactive trigger operation by the gesture of his or her right hand. In the following step S515, the gesture recognition unit 232 analyzes a location of a depth of at least one fingertip of the hand region (i.e., the right-hand region) of the user and tracks a motion trajectory of the at least one fingertip.

Further, the gesture recognition unit 232 analyzes the motion trajectories of the thumb and the index of the hand region (i.e., the right-hand region) of the user (step S517). Through comparing a sample in a gesture interactive semantic database with the depth position of the at least one fingertip of the hand region of the user, the gesture recognition unit 232 recognizes the gesture interactive semantics represented by the motion trajectories (step S519).

Figure 7:
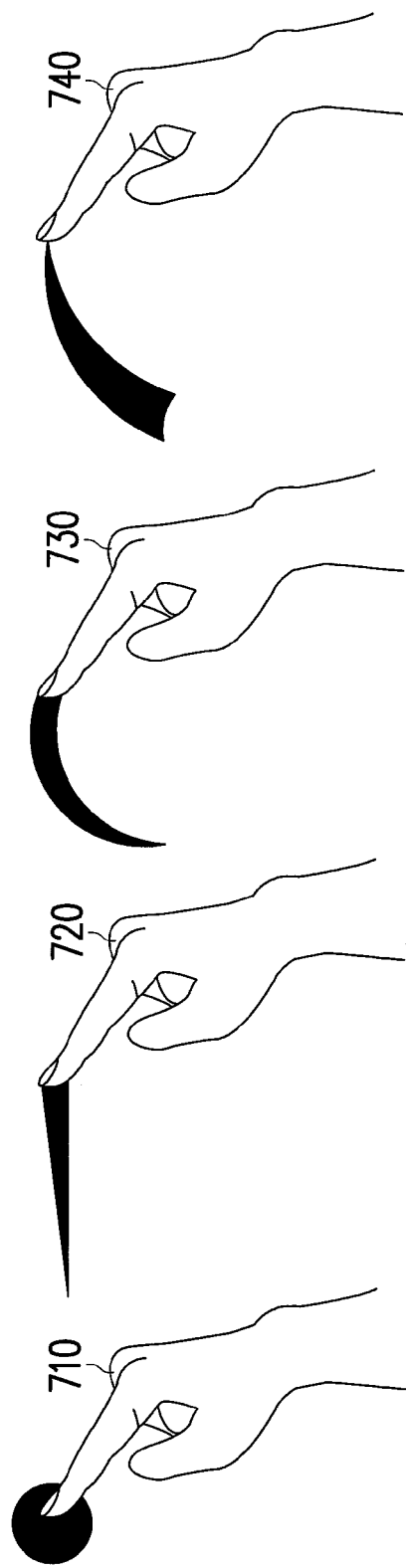
FIG. 7 exemplarily illustrates a sample in a gesture interactive semantic database according to another exemplary embodiment of the disclosure.

In an exemplary embodiment, the establishment of the gesture interactive semantic database is based on several sets of gestures (including basic gestures and the corresponding motion trajectories) as the learning and comparison samples, such as spreading out five fingers, making a fist, picking up or putting down things with fingers, tapping, nudging, spreading-to-enlarge, pinching-to-shrink, and so forth. FIG. 7 exemplarily illustrates a sample in a gesture interactive semantic database according to another exemplary embodiment of the disclosure. For instance, the sample 710 shows that a user taps an object with a fingertip to make selection, and the corresponding gesture interactive semantics are "tap to select"; the sample 720 shows that a finger slides in one direction after the user taps the object with a fingertip to make selection, and the corresponding gesture interactive semantics are "slide to scroll"; the sample 730 shows that a finger spins in a clockwise or a counter-clockwise direction after the user taps the object with a fingertip to make selection, and the corresponding gesture interactive semantics are "spin to scroll", the sample 740 shows that a finger touches and holds an object, slightly moves in a direction, and then leaves the object, and the corresponding gesture interactive semantics are "flick to nudge".

Alternatively, in step S521, the image processing unit 230 outputs the gesture interactive semantics analyzed by the gesture recognition unit 232 to the projection unit 210, such that the projection unit 210 projects the second interactive pattern (e.g., the resultant interactive pattern) corresponding to the gesture interactive semantics. For instance, as shown in FIG. 6C, if the corresponding gesture interactive semantics are "tap to select", the user may tap "1," "2," or "3" to respectively generate different resultant interactive patterns, which may be determined by the user according to the actual requirements. Given that the 3D interactive device 200 is placed in a medical environment, e.g., integrated into an operation lamp, paramedics may tap and select "1" by a gesture, such that the projection unit is allowed to project an indicative pattern (e.g., an arrow pattern) to the body parts of a patient where a surgery is to be performed. The paramedics may continuously interact with the indicative pattern by gestures, e.g., dragging the indicative pattern to other locations, enlarging or shrinking the indicative pattern, and so on. When the paramedics tap and select "2" by a gesture, the projection unit is allowed to project information (e.g., medical history) of a patient, for instance; when the paramedics tap and select "3" by a gesture, the projection unit is allowed to project a surgical flowchart, for instance.

Moreover, the gesture interactive semantics may have one or more corresponding 3D interactive parameters. For instance, the gesture interactive semantics "slide-to-scroll" indicate that the interactive pattern or the object projected by the projection unit is moved together with the movement of the gesture unless the gesture stops moving. However, the speed and the direction of the movement are determined by the 3D interactive parameters. When analyzing and tracking the motion trajectory of the hand region in the depth image, the gesture recognition unit 232 may consider the depth coordinate of the hand region, variations in the depth value, acceleration, and power as the 3D interactive parameters, and the image processing unit 230 may transmit the 3D interactive parameters to the projection unit 210. According to the 3D interactive parameters, the projection unit 210 is allowed to learn the direction where the projected interactive pattern or object is to be moved, the speed of the movement, and so forth. As such, the 3D interactive effects achieved herein may be further enhanced.

To sum up, in the 3D interactive device described in the disclosure, the design of the image capturing unit/device and the design of the projection unit/device are combined, and the technique of calibrating the projection coordinate and the image capturing coordinate is applied, such that the 3D interactive device described herein may position the hand portion of a user in the 3D space, and that the user is allowed to interact with the projected patterns in the 3D space in a contact-free manner. Since the hand portion is recognized and tracked by means of a depth image, the 3D interactive device that experiences environmental changes and background light variations is resistant to light and is able to prevent the ambient light interference. Moreover, if integrated into a medical instrument, the 3D interactive device described herein allows paramedics to input information to the medical device within a hand-sized 3D space in an accurate, contact-free manner, thus lowering the possibility of bacteria infection caused by human contact.

It will be apparent to those skilled in the art that various modifications and variations can be made to the structure of the disclosed embodiments without departing from the scope or spirit of the disclosure. In view of the foregoing, it is intended that the disclosure cover modifications and variations of this disclosure provided they fall within the scope of the following claims and their equivalents.

What is claimed is:

1. A three-dimensional interactive device comprising:
a projection unit projecting a first interactive pattern to a surface of a body, such that a user performs an interactive trigger operation on the first interactive pattern by a gesture, wherein the first interactive pattern is projected within a projection range;
an image capturing unit capturing a depth image within an image capturing range, wherein the image capturing range covers the projection range; and
an image processing unit connected to the projection unit and the image capturing unit, the image processing unit receiving the depth image and determining whether the depth image comprises a hand region of the user, if yes, the image processing unit performs hand geometric recognition on the hand region to obtain a gesture interactive semantics, and the image processing unit controls the projection unit and the image capturing unit according to the gesture interactive semantics.

2. The three-dimensional interactive device as recited in claim 1, wherein the projection unit projects a border marker symbol and a center marker symbol on at least one border point and a center of the projection range, respectively, so as to form a calibration pattern for calibration.

3. The three-dimensional interactive device as recited in claim 2, further comprising:
a coordinate calibration unit coupled to the projection unit and the image capturing unit, the coordinate calibration unit receiving a three-primary-color image captured by the image capturing unit, wherein the three-primary-color image covers the calibration pattern, the coordinate calibration unit analyzes a coordinate of the border marker symbol and a coordinate of the center marker symbol in the three-primary-color image through conducting an image comparison method to obtain a coordinate transformation between a projection coordinate of the projection unit and an image capturing coordinate of the image capturing unit.

4. The three-dimensional interactive device as recited in claim 2, wherein the border marker symbol projected by the projection unit is a pattern of a circular point.

5. The three-dimensional interactive device as recited in claim 2, wherein the center marker symbol projected by the projection unit is a hand-shaped pattern.

6. The three-dimensional interactive device as recited in claim 1, wherein the image processing unit further comprises:
a gesture recognition unit analyzing the depth image through conducting a histogram statistical method and recognizing the hand region of the user through a convex hull and a convex deficiency of the depth image.

7. The three-dimensional interactive device as recited in claim 6, wherein the gesture recognition unit further recognizes a location of a centroid point of the hand region of the user and outputs a coordinate of the centroid point corresponding to the location of the centroid point to the projection unit.

8. The three-dimensional interactive device as recited in claim 7, wherein the projection unit correspondingly adjusts a projection location of a second interactive pattern and a dimension of the second interactive pattern according to the coordinate of the centroid point.

9. The three-dimensional interactive device as recited in claim 6, wherein the gesture recognition unit further recognizes a depth position of at least one fingertip of the hand region of the user and tracks a motion trajectory of the at least one fingertip, and the gesture recognition unit recognizes the gesture interactive semantics represented by the motion trajectory through comparing a sample in a gesture interactive semantic database with the depth position of the at least one fingertip of the hand region of the user.

10. The three-dimensional interactive device as recited in claim 9, wherein the gesture recognition unit transmits the gesture interactive semantics and at least one three-dimensional interactive parameter obtained by analyzing the depth position of the at least one fingertip and the motion trajectory to the projection unit and the image capturing unit, so as to control the projection unit to project a second interactive pattern corresponding to the gesture interactive semantics and control the image capturing unit to continuously capture the depth image comprising the gesture.

11. The three-dimensional interactive device as recited in claim 1, wherein the gesture interactive semantics at least comprise a tap-to-select operation, a slide-to-scroll operation, a spin-to-scroll operation, a flick-to-nudge operation, a spread-to-enlarge operation, and a pinch-to-shrink operation.

12. The three-dimensional interactive device as recited in claim 1, wherein the projection unit is a pico-projector.

13. The three-dimensional interactive device as recited in claim 1, wherein the image capturing unit is a time-of-flight camera, a stereo vision depth camera, a laser speckle camera, or a laser tracking camera.

14. An operation method of a three-dimensional interactive device, the three-dimensional interactive device comprising a projection unit and an image capturing unit, the operation method comprising:
 performing a coordinate calibration process on a projection coordinate of the projection unit and an image capturing coordinate of the image capturing unit;
 projecting a first interactive pattern to a surface of a body by the projection unit, such that a user performs an interactive trigger operation on the first interactive pattern by a gesture, wherein the first interactive pattern is projected within a projection range;
 capturing a depth image within an image capturing range by the image capturing unit, wherein the image capturing range covers the projection range;
 determining whether the depth image comprises a hand region of the user; if yes, performing a hand geometric recognition on the hand region to obtain a gesture interactive semantics; and
 controlling the projection unit and the image capturing unit according to the gesture interactive semantics.

15. The operation method as recited in claim 14, wherein the coordinate calibration process comprises:
 respectively projecting a border marker symbol and a center marker symbol on at least one border point and a center of the projection range by the projection unit, so as to form a calibration pattern;
 capturing a three-primary-color image of the calibration pattern by the image capturing unit; and
 analyzing a coordinate of the border marker symbol and a coordinate of the center marker symbol in the three-primary-color image through conducting an image comparison method to obtain a coordinate transformation between the projection coordinate and the image capturing coordinate.

16. The operation method as recited in claim 15, wherein the border marker symbol is a pattern of a circular point.

17. The operation method as recited in claim 15, wherein the center marker symbol is a hand-shaped pattern.

18. The operation method as recited in claim 14, wherein the step of determining whether the depth image comprises the hand region of the user to obtain the gesture interactive semantics comprises:
 analyzing the depth image through conducting a histogram statistical method;
 recognizing the hand region of the user through a depth value of the depth image as well as a convex hull and a convex deficiency of the depth image; and
 recognizing a location of a depth of at least one fingertip of the hand region of the user, tracking a motion trajectory of the at least one fingertip, and recognizing the gesture interactive semantics represented by the motion trajectory through comparing a sample in a gesture interactive semantic database with the depth position of the at least one fingertip of the hand region of the user.

19. The operation method as recited in claim 18, after obtaining the gesture interactive semantics, the operation method further comprising:
 transmitting at least one three-dimensional interactive parameter obtained by analyzing the depth position of the at least one fingertip and the motion trajectory to the projection unit and the image capturing unit, so as to control the projection unit to project a second interactive pattern corresponding to the gesture interactive semantics and control the image capturing unit to continuously capture the depth image comprising the gesture.

20. The operation method as recited in claim 19, further comprising:
 recognizing a location of a centroid point of the hand region of the user and outputting a coordinate of the centroid point corresponding to the location of the centroid point to the projection unit; and
 according to the coordinate of the centroid point, correspondingly adjusting a projection location of the second interactive pattern and a dimension of the second interactive pattern by the projection unit.

21. The operation method as recited in claim 14, wherein the gesture interactive semantics at least comprise a tap-to-select operation, a slide-to-scroll operation, a spin-to-scroll operation, a flick-to-nudge operation, a spread-to-enlarge operation, and a pinch-to-shrink operation.

* * * * *